United States Patent
Chandrasekaran et al.

(10) Patent No.: US 6,451,037 B1
(45) Date of Patent: Sep. 17, 2002

(54) EXPANDABLE ATHERECTOMY BURR WITH METAL REINFORCEMENT

(75) Inventors: Verivada Chandrasekaran, Mercer Island; Thomas J. Hiblar, Everett, both of WA (US)

(73) Assignee: SCIMED Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/721,349

(22) Filed: Nov. 22, 2000

(51) Int. Cl.[7] .............................................. A61B 17/32
(52) U.S. Cl. ........................ 606/159; 606/170; 606/180
(58) Field of Search ............................. 606/1, 108, 159, 606/167, 170, 171, 180, 198; 604/22, 96.01, 103.08, 103.09, 104; 600/562–571; 428/544

(56) References Cited

U.S. PATENT DOCUMENTS

| | | |
|---|---|---|
| 2,701,559 A | 2/1955 | Cooper |
| 3,614,953 A | 10/1971 | Moss |
| 3,896,815 A | 7/1975 | Fettel et al. |
| 4,273,128 A | 6/1981 | Lary |
| 4,465,072 A | 8/1984 | Taheri |
| 4,589,412 A | 5/1986 | Kensey |
| 4,631,052 A | 12/1986 | Kensey |
| 4,653,496 A | 3/1987 | Bundy et al. |
| 4,685,458 A | 8/1987 | Leckrone |
| 4,696,667 A | 9/1987 | Masch |
| 4,706,670 A | 11/1987 | Andersen et al. |
| 4,728,319 A | 3/1988 | Masch |
| 4,747,821 A | 5/1988 | Kensey et al. |
| 4,765,332 A | 8/1988 | Fischell et al. |
| 4,781,186 A | 11/1988 | Simpson et al. |
| 4,784,636 A | 11/1988 | Rydell |
| 4,794,928 A | 1/1989 | Kletschka |
| 4,794,931 A | 1/1989 | Yock |
| 4,842,579 A | 6/1989 | Shiber |
| 4,857,045 A | 8/1989 | Rydell |
| 4,886,061 A | * 12/1989 | Fischell et al. |
| 4,898,574 A | 2/1990 | Uchiyama et al. |
| 4,926,858 A | 5/1990 | Gifford, III et al. |

(List continued on next page.)

FOREIGN PATENT DOCUMENTS

| | | |
|---|---|---|
| DE | 867144 | 2/1953 |
| EP | 0 086 048 A2 | 8/1983 |
| EP | 0 204 218 A1 | 12/1986 |

*Primary Examiner*—Michael J. Milano
*Assistant Examiner*—(Jackie) Tan-Uyen T. Ho
(74) *Attorney, Agent, or Firm*—Christensen O'Connor Johnson Kindness PLLC (57) ABSTRACT

An atherectomy burr having an operating diameter that is larger than the diameter of a catheter in which the burr is routed. The burr may include a flexible polymeric tube that is plated with an abrasive and that expands when the burr is rotated. Metal fibers are embedded into burr to improve strength and to control the maximum expansion diameter of the burr. The abrasive is plated on the burr by first selectively exposing the underlying metal. The exposed metal is then plated with a layer of metal such as nickel having a slurry of diamond particles disposed therein using an electro and/or electroless plating method. When the burr is rotated, the polymeric tube expands by centrifugal force to ablate a new lumen in the patient's vessel.

23 Claims, 5 Drawing Sheets

U.S. PATENT DOCUMENTS

| | | |
|---|---|---|
| 4,950,238 A | 8/1990 | Sullivan |
| 4,966,604 A | 10/1990 | Reiss |
| 4,990,134 A | 2/1991 | Auth |
| RE33,569 E | 4/1991 | Gifford, III et al. |
| 5,030,201 A | 7/1991 | Palestrant |
| 5,100,425 A * | 3/1992 | Fischell et al. |
| 5,152,773 A * | 10/1992 | Redha |
| 5,154,724 A * | 10/1992 | Andrews |
| 5,192,291 A | 3/1993 | Pannek, Jr. |
| 5,224,945 A | 7/1993 | Pannek, Jr. |
| 5,250,060 A | 10/1993 | Carbo et al. |
| 5,318,576 A * | 6/1994 | Plassche, Jr. et al. |
| 5,342,307 A | 8/1994 | Euteneuer et al. |
| 5,376,100 A | 12/1994 | Lefebvre |
| 5,385,311 A | 1/1995 | Morikawa et al. |
| 5,395,311 A | 3/1995 | Andrews |
| 5,456,666 A | 10/1995 | Campbell et al. |
| B1 4,842,579 A | 10/1995 | Shiber |
| 5,490,859 A * | 2/1996 | Mische et al. |
| 5,556,405 A | 9/1996 | Lary |
| 5,569,276 A | 10/1996 | Jang et al. |
| 5,571,086 A | 11/1996 | Kaplan et al. |
| B1 4,990,134 A | 11/1996 | Auth |
| 5,649,941 A | 7/1997 | Lary |
| 5,653,696 A | 8/1997 | Shiber |
| 5,681,336 A | 10/1997 | Clement et al. |
| 5,725,543 A | 3/1998 | Redha |
| 5,725,568 A | 3/1998 | Hastings |
| 5,749,914 A | 5/1998 | Janssen |
| 5,766,192 A | 6/1998 | Zacca |
| 5,842,479 A | 12/1998 | Plaia et al. |
| 6,096,054 A | 8/2000 | Wyzgala et al. |
| 6,156,046 A * | 12/2000 | Passafaro et al. |

* cited by examiner

Fig. 4.

EXPANDABLE ATHERECTOMY BURR WITH METAL REINFORCEMENT

FIELD OF THE INVENTION

The present invention relates to medical devices in general, and in particular to atherectomy devices for removing occluding material from a patient's blood vessels.

BACKGROUND OF THE INVENTION

Arteriosclerosis is a common vascular disease in which a patient's blood vessels become hardened and blocked by plaque or clots that impede blood flow. Left untreated, this condition is a major contributing factor to the occurrence of high blood pressure, strokes and cardiac arrest.

Many invasive and non-invasive techniques have been developed to treat arteriosclerosis. For example, cardiac bypass surgery is now a commonly performed procedure whereby an occluded cardiac artery is bypassed with a segment of a healthy blood vessel that is obtained from elsewhere in the body. While this procedure is generally successful, it is fairly traumatic because the entire chest cavity must be opened to access the occluded vessel. Therefore, the procedure is not generally performed on elderly or relatively frail patients.

One example of a promising minimally invasive technique that can be performed on a greater number of patients is to remove the occluding material from a patient's vessel in an atherectomy procedure. To perform this procedure, a guide catheter is typically inserted into the patient's femoral artery and advanced until the distal end of the guide catheter is located in the patient's ostium. A guide wire is then inserted through the guide catheter and traversed into the coronary arteries and past the occluded material to be treated. Then, as described in U.S. Pat. No. 4,990,134, issued to Auth, an atherectomy catheter having a small abrasive burr is advanced through the guide catheter and over the guide wire to the point of the occlusion. The burr is then rotated at high speed and passed through the occlusion to remove particles that are sufficiently small such that they will not re-embolize in the distal vasculature. As the burr removes the occlusion, a larger lumen is created in the vessel and blood flow is restored.

It is well recognized that the risk of certain patient complications increases with the size of the guide catheter through which minimally invasive devices are routed. Larger guide catheters require larger access holes in the femoral artery, creating the potential for patient complications, such as the sealing of the puncture site after completion of the procedure. Therefore, physicians generally wish to utilize the smallest possible guide catheter during a procedure. However, the smaller size guide catheters can only accommodate corresponding smaller size ablation burrs. Therefore, if a large vessel is to be treated, a larger burr and corresponding larger guide catheter must be used to successfully remove all of the occlusion from the patient's vessel.

In addition, it has also been discovered that when performing an atherectomy procedure as described earlier, it has been beneficial to remove only a small amount of the occlusion at a time. Therefore, currently many procedures are performed using multiple passes through the occlusion with different sized ablation burrs. While these procedures have proven effective, the use of multiple devices for a single procedure adds both time and cost to the procedure.

One solution to the above mentioned problems associated with the existing atherectomy devices have been addressed by the development of an atherectomy device that can treat different size vessels while being traversed through a small guide catheter. This has been achieved by using a burr with a polymeric tube section that expands due to mechanical, hydraulic, or rotational means. An abrasive material is coated to the outside of the burr to provide a textured surface that can ablate the occlusion in a patient's vessel.

However, the advances in development of atherectomy burr devices have created several difficulties in making and using the expandable burr device. The polymeric tube section of conventional expandable burr devices have been plated with an abrasive material using common plating techniques such as high-vacuum plasma deposition. However, these techniques are expensive, extremely complicated, and provide less adhesion between the abrasive and the polymeric substrate than generally desired. Further, it has been difficult to control the degree of expansion of the polymeric material, resulting in over-expansion of the burr at high rotational speeds. Over-expansion of the burr may stretch the burr beyond its elastic range resulting in a permanent, non-recovery deformation of the burr. Therefore, there is a need for an improved burr with the ability to expand to a predetermined maximum diameter during the operation of the burr while further providing an improved and more economical method of securing the abrasive material to the outside of the burr.

SUMMARY OF THE INVENTION

To eliminate the need for a physician to utilize larger guide catheters in order to route a larger diameter ablation burr in a patient, while solving the abovementioned deficiencies of the conventional expandable burr, the present invention comprises an improved expandable ablation burr including a flexible material with metal reinforcement fibers embedded therein. The expandable ablation burr is coated with an abrasive to ablate a new lumen in a patient's vessel. The ablated diameter of the patient's vessel preferably has a diameter that exceeds the diameter of a guide catheter through which the burr is routed.

According to one aspect of the present invention, the ablation burr comprises a flexible polymeric tube that expands as the burr is rotated. Metal reinforcement fibers are embedded within the tube to control the shape of the tube during expansion and to provide a predetermined maximum diameter of the expandable burr. The size of the burr changes in accord with the centrifugal force that is developed during rotation of the burr. Metal reinforcement fiber within the flexible polymeric tube improves the strength of the burr while preventing over-expansion of the burr.

In another aspect of the invention, the ablation burr comprises a flexible polymeric tube that is coated with an abrasive material. Metal reinforcement fibers within the polymeric tubing are exposed to allow the plating of the abrasive material to the tube. A portion of the exposed reinforcement is plated with an abrasive such that the tube will ablate an occlusion as the burr is rotated and advanced through a vessel. Plating metal is more economical than plating a polymer and provides a greater adhesion force between the abrasive coating and the burr. As the burr is rotated, the elastomeric tube expands by centrifugal force, thereby increasing the maximum outer diameter of the burr in order to create a larger lumen in a patient's vessel.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

As will be explained in further detail below, the present invention is an ablation burr having an outer diameter that may be expanded to exceed the diameter of a guide catheter through which the burr is routed. The burr of the present invention is reinforced by metal fibers to strengthen the burr and to provide the burr with a predetermined maximum diameter during expansion. The metal reinforcement fiber further aids in serving as a substrate for plating the abrasive on the burr.

Figure 1:
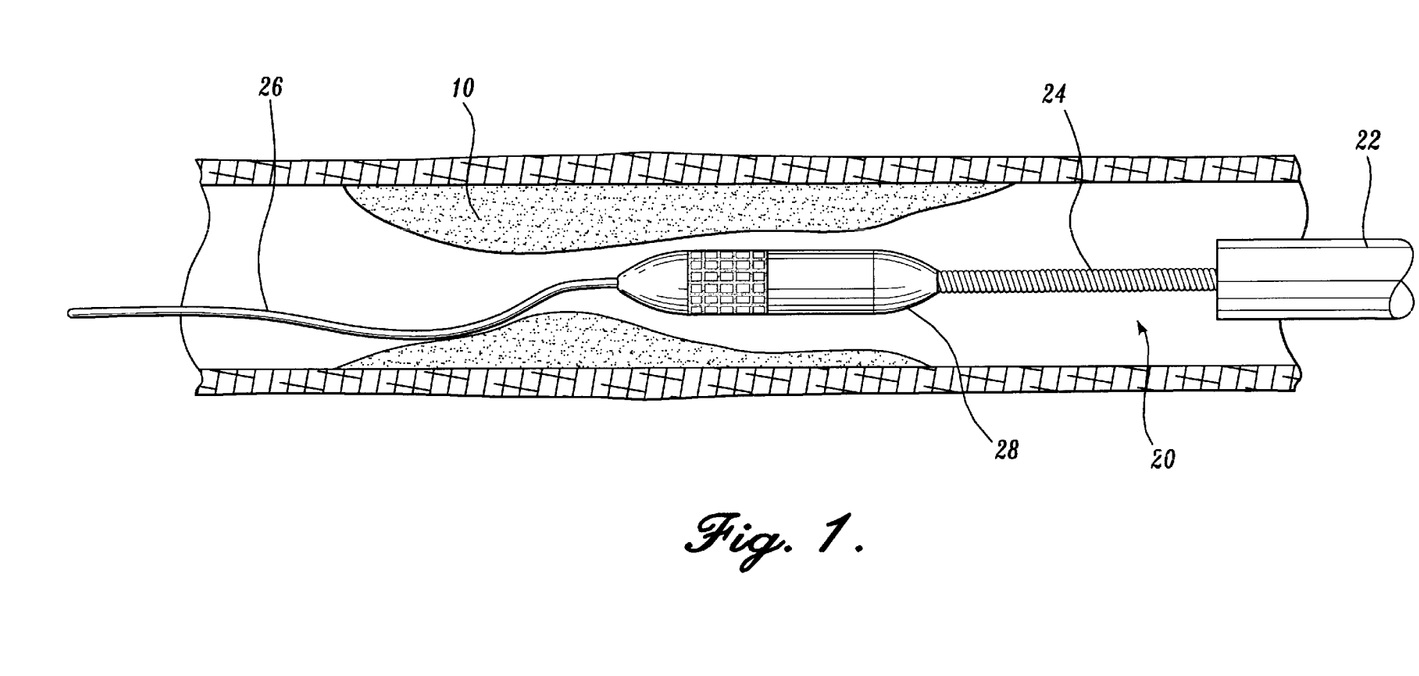
FIG. 1 illustrates an expandable ablation burr including a mechanism for the predetermining and controlling the maximum outer diameter of the burr according to an aspect of the present invention.

FIG. 1 illustrates an ablation burr according to a first aspect of the present invention. The atherectomy device 20 is routed from a position outside a patient's body to a point near the site of a vascular occlusion 10 through a guide catheter 22. Extending through the guide catheter 22 is a drive shaft 24 that is coupled at its proximal end to a source of rotational motion such as an electric motor or gas turbine (not shown) that rotates the drive shaft 24 at high speed, e.g., between 20,000 and 250,000 rpm. Disposed at a distal end of the drive shaft 24 is an ablation burr 28 that when rotated by the drive shaft 24 to ablate a new lumen through the occlusion in order to permit blood to flow more freely through the vessel. Extending through the drive shaft 24 and the ablation burr 28 is a guide wire 26 that can be steered by a physician in order to guide the ablation burr through the vascular occlusion 10.

Figures 2, 3:
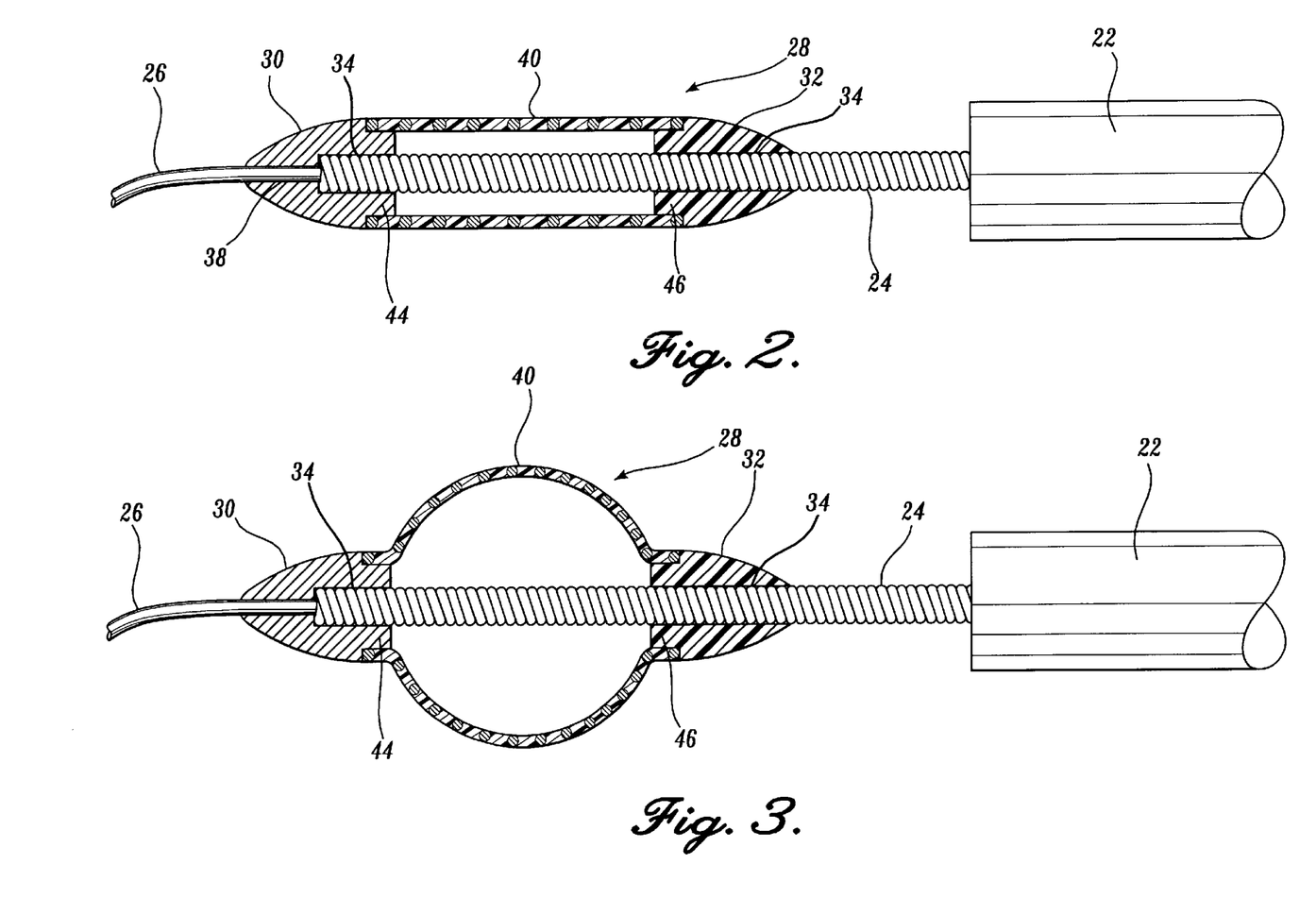
FIG. 2 illustrates a cross-sectional view of the expandable ablation burr of FIG. 1 having a mechanism for predetermining and controlling the maximum outer diameter of the burr according to an aspect of the present invention.
FIG. 3 illustrates a cross-sectional view of the expandable ablation burr of FIG. 1 having a mechanism for predetermining and controlling the maximum outer diameter of the burr according to an aspect of the present invention in its expanded state.
Figure 4:
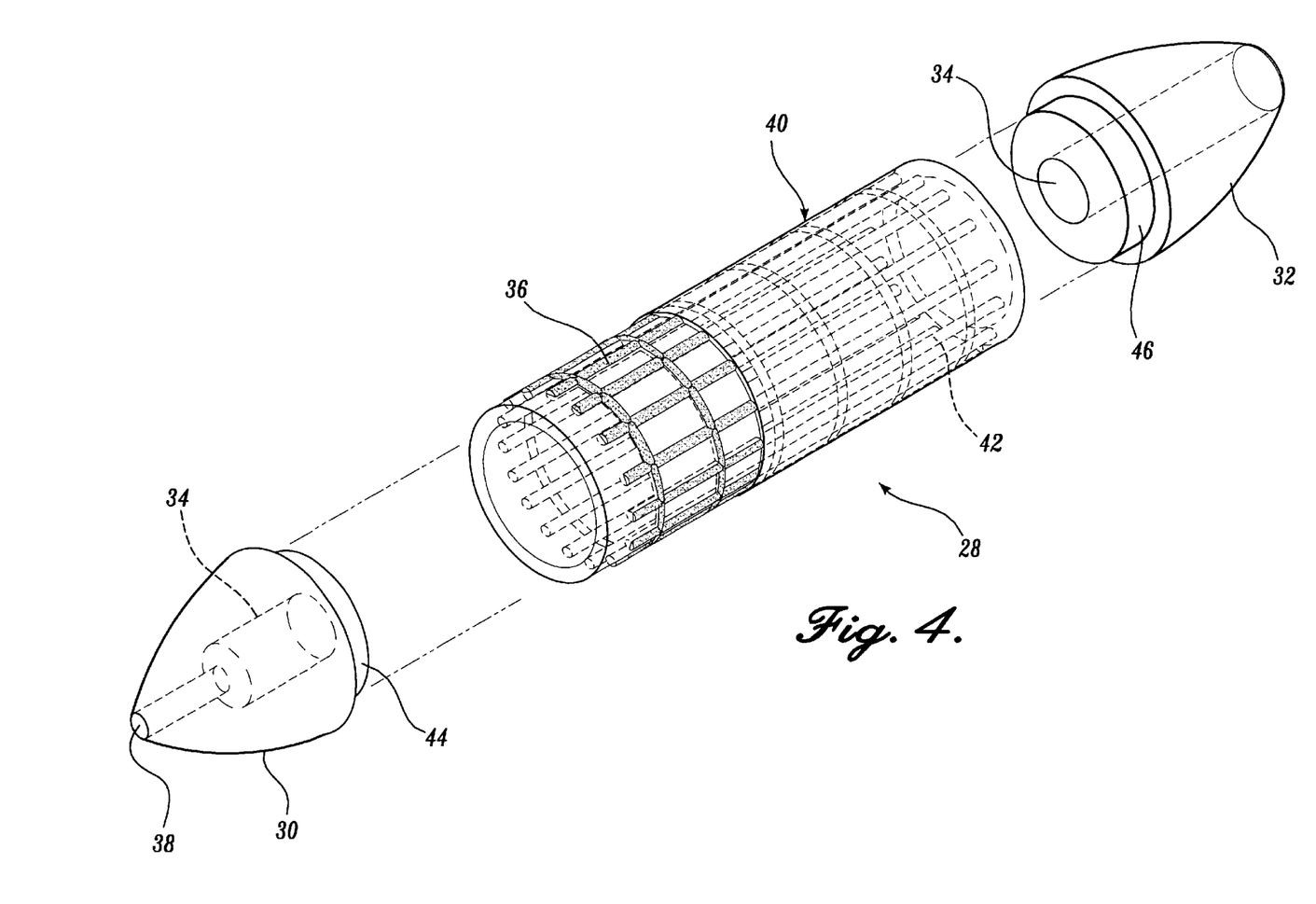
FIG. 4 illustrates an assembly view of an expandable ablation burr of FIG. 1 having a mechanism for predetermining and controlling the maximum outer diameter of the burr according to an aspect of the present invention in its expanded state.

As best shown in FIGS. 2–4, the expandable ablation burr 28 comprises a bullet-shaped leading nose section 30 coupled to the distal end of a flexible drive shaft 24 and a similarly shaped proximal end section 32 in sliding engagement over drive shaft 24. A central lumen 34 extends through end section 32 and an adjacent portion of nose section 30 to accommodate drive shaft 24. Nose section 30 is preferably made from a metal material such as brass or the like and is bonded to the drive shaft 24 by an adhesive such as epoxy or the like. Nose section 30 has a maximum diameter that begins proximally and tapers in size to the distal tip of the burr. Nose section 30 further includes a proximal stepped portion or shoulder 44 having a diameter that is less than the maximum diameter of the nose section 30. Located at the distal end of nose section 30 and having a smaller diameter than central lumen 34 is guide wire lumen 38. Guide wire lumen 38 extends through the tip of nose section 30 so that the ablation burr may be threaded over guide wire 26.

The proximal end section 32 of the ablation burr 28 is preferably made from a polymeric material such as polyurethane or the like and has a maximum diameter that begins distally and tapers in size to the proximal tip of the burr. The end section 32 further contains a distal stepped portion or shoulder 46 having a diameter that is less than the maximum diameter of the end section 32. The proximal end section 32 may be bonded to the drive shaft 24 so that end section 32 rotates with the drive shaft to prevent the tube section from twisting. In an embodiment that does not bond the end section 32 to the drive shaft 24, the inner surface of end section 32 includes a rotational lock, which is described in detail below, so that the end section can slide axially along the drive shaft 24 but cannot rotate separately from drive shaft 24. Therefore, any torque induced by the drive shaft 24 will be transmitted to end section 32.

The rotational lock (not shown) is comprised of a square shaped bore that extends through end section 32 and a drive shaft with a corresponding shape matable with end section 32 so that the rotational motion of the drive shaft is transferred thereto. A square shaped metal tube can be bonded to the drive shaft 24 or the drive shaft 24 can be crimped, ground to a square or otherwise formed to provide the corresponding shape to rotate end section 32. It should be appreciated to one of ordinary skill that other structures may be used to provide the features of the rotational lock such as a pin/slot arrangement.

Still referring to FIGS. 2–4, coupled between the stepped portions 44, 46 of nose and end sections 30, 32 is a tube or sheath section 40 having an abrasive 36 (FIG. 4) disposed thereon. Tube section 40 is made from a stretchable polymeric or elastomeric material such as polyurethane or polyethylene. However, it is believed that other plastics or elastomeric materials may also be used. Reinforcement fibers 42 are embedded into the tube section 40 to improve the overall strength of the burr and to provide a mechanism for controlling the shape of the burr during expansion and for restricting the expansion of the burr to a maximum diameter so that the burr does not over-expand.

The reinforcement fibers 42 are made from a metal, preferably of a medium to high strength, such as stainless steel or titanium. The polymeric tube with embedded metal reinforcement is made by known fabrication techniques such as molding, casting, extrusion, or the like. The reinforcement may be configured in any shape or pattern that can control the shape of the burr during expansion and provide a maximum expansion diameter. In one embodiment, as shown in FIG. 5, the reinforcement fibers 42 are configured in a grid or cross-ply pattern having columns 60 of fibers that extend longitudinally, preferably from the proximal end of the tube section to the distal end of the tube section in spaced relation, and having circular loops 62 of fiber that extend circumferentially around the tube section, perpendicular to the longitudinally extending columns of fiber.

Figures 5, 6:
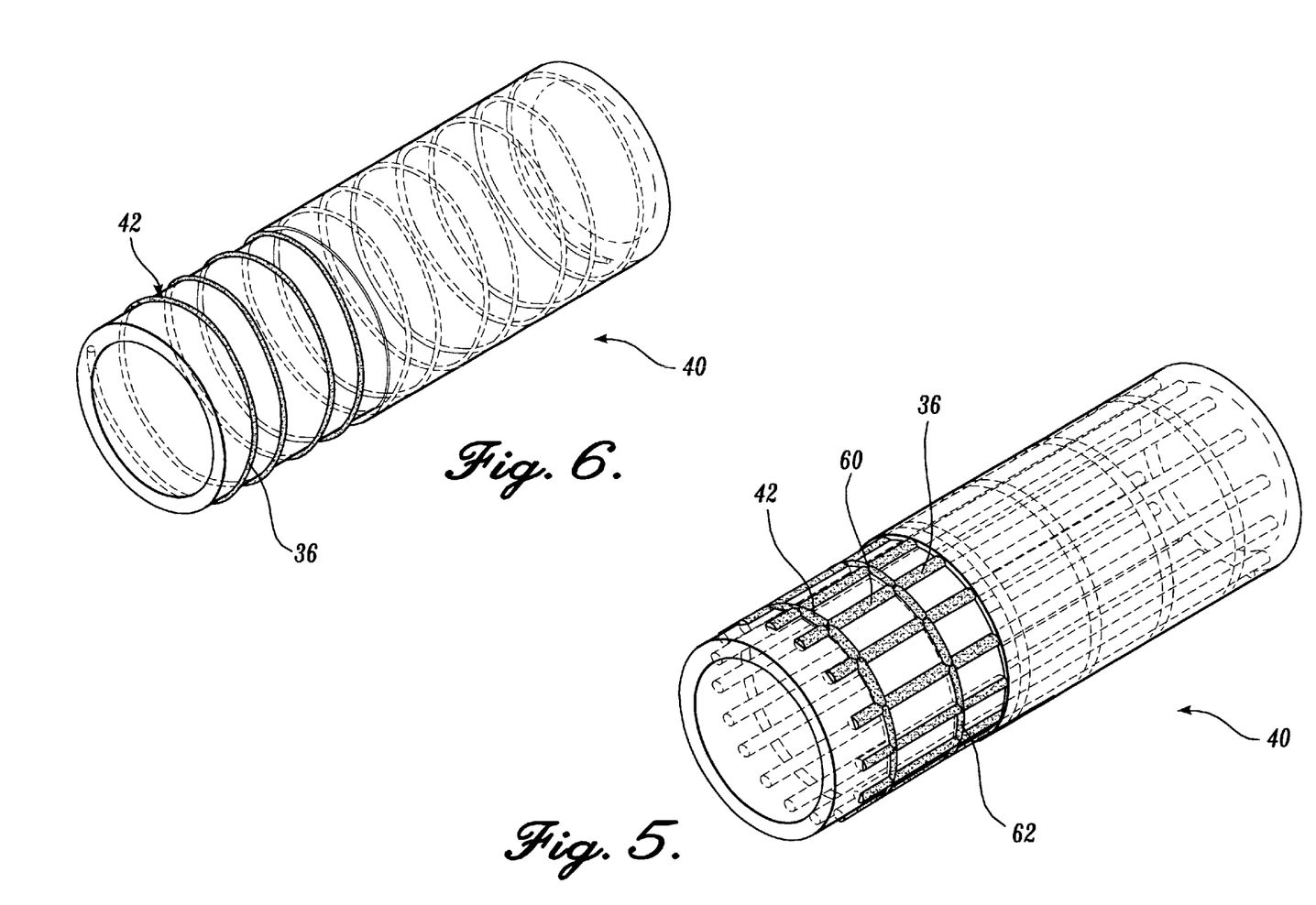
FIGS. 5 illustrates in fragmentary view a tube section of an expandable ablation burr including a mechanism for predetermining and controlling the maximum outer diameter of the burr according to an aspect of the present invention.
FIGS. 6 illustrates in fragmentary view another embodiment of a tube section of the expandable ablation burr including a mechanism for predetermining and controlling the maximum outer diameter of the burr according to the present invention.
Figures 7, 8:
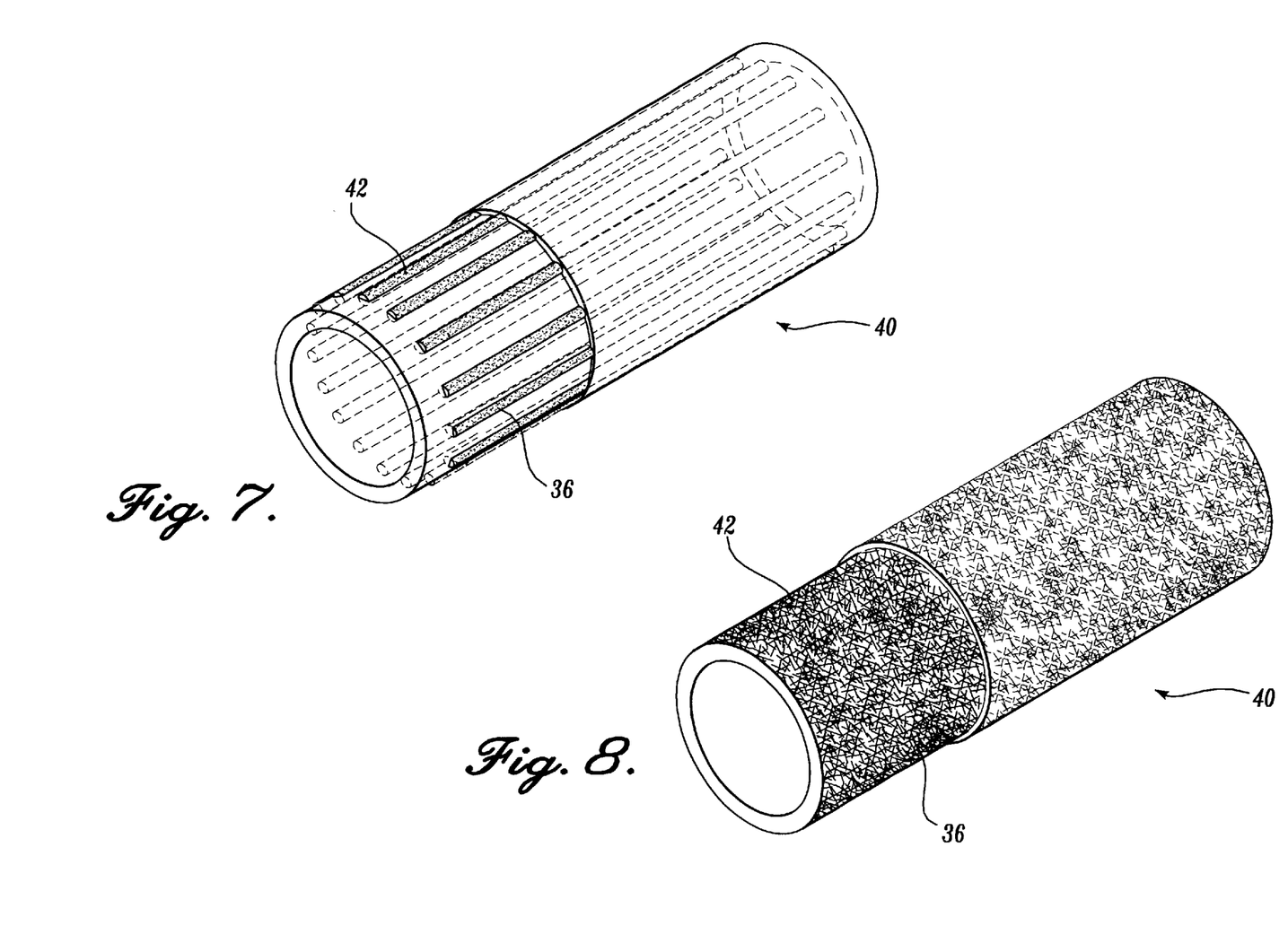
FIGS. 7 illustrates in fragmentary view yet another embodiment of a tube section of the expandable ablation burr including a mechanism for predetermining and controlling the maximum outer diameter of the burr according to the present invention.
FIGS. 8 illustrates in fragmentary view still yet another embodiment of a tube section of the expandable ablation burr including a mechanism for predetermining and controlling the maximum outer diameter of the burr according to the present invention.

Alternatively, as shown in FIGS. 6–8, the ablation burr may include a tube section 40 having embedded fibers 42 wherein the metal fibers are configured in spiral, uni-directional, or random patterns, respectively. The random pattern shown in FIG. 8 requires that all of the fibers 42 are in contact with one another so that an electrical charge can be established in the fiber during the plating process.

FIGS. 2 and 3 illustrate the ablation burr 28 as the drive shaft 24 is rotated. Centrifugal force causes a center section of the polymeric tube that lies between the proximal end of the nose section 30 and the distal end of the end section 32 to expand radially outward. As the burr begins spinning fast enough, centrifugal force expands the polymeric tube 40. Fluid then fills the interior cavity of the tube through drive shaft 24 and is also acted on by the centrifugal force. As the tube section expands radially outward, the embedded reinforcement fibers 42 control and restrict the expansion of the burr so as to maintain a substantially uniform elliptical shape. If the rotational speed of the burr continues to increase, the tube section attempts to further expand. However, the embedded fibers prevent the further expansion and restrain the burr to a maximum expansion diameter. As the rotational speed of the ablation burr is decreased, the outer diameter of the burr decreases so that the burr can be withdrawn through the catheter. The dimensions and pattern of the metal reinforcement is determined by the mechanical requirements (i.e. strength, durability, weight) of the composite burr and can be used to determine the maximum expansion diameter of the burr.

In conjunction with the various reinforcement configurations as described in FIGS. 5–8, the abrasive is secured to the ablation burr in accordance with another aspect of the present invention. The abrasive 36 is secured to the tube section by ablating with lasers or abrading mechanically to remove a very localized area (i.e. 100–200 microns) of the outer layer of the tube section 40 that covers or overlays the reinforcement fibers 42 to expose the underlying metal. Once the portions of the outer layer of the polymer tube section 40 is removed, the exposed metal fibers, serving as the substrate, are plated with a layer of metal such as nickel, having a slurry of diamond particles suspended therein, using an electro and/or electroless plating method. The abrasive 36 deposited on the outer surface of the tube preferably comprises small diamond chips approximately 2–60 microns in size. In some instances, it may be desirable to selectively remove a portion of the of the tube section in a pattern of dots or other shapes so that the abrasive does not completely cover the metal fiber to prevent an excessive amount of abrasive deposited on the burr.

As will be appreciated by those skilled in the art, polymeric tube 40 is expanded by centrifugal force generated by the rotation of drive shaft 24. However, other suitable means of expanding the tube known in the art such as hydraulically, or self-expanding, may be employed. For example, the reinforcement fiber used in the various embodiments of the tube section of the expandable burr described above can be a memory metal such as nickel titanium. The reinforcement fiber using a memory metal will assume its final diameter (or shape) after it is released from the guide catheter. The maximum expansion diameter of the ablation burr can easily be predetermined. This provides the physician with the flexibility of choosing the final diameter expandable burr best suited for each individual patient.

In some instances, it may be desirable to coat the outer surface of the polymeric tube with a hydrophilic coating such as HydropassTM, available from Boston Scientific and described in U.S. Pat. No. 5,702,754. The hydrophilic coating attracts water molecules, thereby making the surface slippery and easier to advance along the guide catheter. In addition, the hydrophilic coating may be beneficial during ablation since less torque may be transferred to a vessel wall if the burr stalls. In addition, the differential cutting ability of the burr may be enhanced due to the increased ability of the burr to slide over soft tissues.

As can been seen from the above description, the present invention provides a mechanism for controlling the maximum diameter of an ablation burr. By controlling the maximum diameter of the burr, an expandable ablation burr may be used in order to ablate a larger diameter lumen in a patient. The present invention further provides an improved method of plating the abrasive material to the ablation burr. Plating the abrasive on the exposed metal fiber is less expensive, less complicated, and provides better adhesion between the abrasive coating and the burr than when plating an abrasive to a polymer.

While the preferred embodiments of the invention has been illustrated and described, it will be appreciated that various changes can be made therein without departing from the spirit and scope of the invention. For example, the fiber patterns embedded into the polymeric material have been shown in a cross-ply, spiral, unidirectional, and random configuration; however, the fiber pattern may vary. It may be desirable to have the pattern sinusoidal, parabolic, hyperbolic, or any other suitable pattern that will provide a maximum diameter of the expanding tube. The scope of the invention should therefore be determined from the following claims and equivalents thereto.

The embodiments of the invention in which an exclusive property or privilege is claimed are defined as follows:

1. An atherectomy device for ablating an occlusion in a patient's blood vessel, comprising:
    a drive shaft;
        an ablation burr having a proximal end and a distal end secured to the drive shaft, the ablation burr including:
        a polymeric tube extending from the proximal end of the ablation burr to the distal end of the ablation burr, the polymeric tube having an unexpanded state with a first diameter and an expanded state with a second larger diameter;
        metal fibers affixed to the polymeric tube and operable to reinforce the polymeric tube; and
        an abrasive coating disposed on at least a portion of the exterior surface of the ablation burr to ablate an occlusion in a patient's vessel; and
    a lumen extending through the drive shaft and ablation burr for receiving a guide wire.

2. The atherectomy device of claim 1, wherein the metal fiber is embedded in the polymeric tube.

3. The atherectomy device of claim 2, wherein the metal fiber has a cross-ply configuration.

4. The atherectomy device of claim 2, wherein the metal fiber has a unidirectional configuration.

5. The atherectomy device of claim 2, wherein the metal fiber has a spiral configuration.

6. The atherectomy device of claim 2, wherein the metal fiber has a random configuration.

7. The atherectomy device of claim 2, wherein the metal fiber determines the second larger diameter of the burr by restricting the expansion thereof.

8. The atherectomy device of claim 2, wherein the metal fiber prevents over expansion of the tube.

9. The atherectomy device of claim 2, wherein the metal fiber controls the expansion of the tube.

10. The atherectomy device of claim 2, wherein a portion of the tube is removed to expose the metal fiber.

11. The atherectomy device of claim 10, wherein the abrasive is disposed on the exposed metal fiber.

12. The atherectomy device of claim 1, wherein the abrasive is disposed on the metal fiber.

13. The atherectomy device of claim 1, wherein the polymeric tube is made of a stretchable plastic material.

14. The atherectomy device of claim 1, wherein the polymeric tube assumes the expanded state when rotated by the drive shaft.

15. An atherectomy device for ablating an occlusion in a patient's blood vessel, comprising:
 a drive shaft;
 an ablation burr secured to the drive shaft, the burr including a nose section having a fixed maximum diameter, a polymeric section having metal fibers, and an abrasive disposed on at least a portion the burr, the polymeric section having a diameter that increases as a result of the burr being rotated by the drive shaft; and
 a lumen extending through the drive shaft and ablation burr for receiving a guide wire.

16. The atherectomy device of claim 15, wherein the nose section further comprises a stepped section of a substantially constant diameter that is smaller than the maximum diameter of the nose section, and wherein the polymeric section comprises a polymeric tube section engaged over the stepped section.

17. The atherectomy device of claim 15, wherein the metal fibers are embedded within the polymeric section.

18. The atherectomy device of claim 17, wherein a portion of the polymeric tube is removed to expose the metal fiber, the abrasive being disposed on the metal fibers.

19. The atherectomy device of claim 15, wherein the metal fibers restrict the expansion of the burr.

20. An atherectomy device for ablating an occlusion in a patient's blood vessel, comprising:
 a drive shaft;
 an ablation burr secured to the drive shaft, the burr including:
  a nose section having a fixed maximum diameter; and
  a polymeric section having embedded metal fibers operable to reinforce the polymeric tube, the outer surface of the embedded metal fibers having a cutting surface thereon; wherein the polymeric section has an unexpanded state with a first diameter and an expanded state with a second larger diameter; and
 a lumen extending through the drive shaft and the ablation burr for receiving a guide wire.

21. The atherectomy device of claim 20, wherein the cutting surface is an abrasive coating.

22. The atherectomy device of claim 20, wherein the embedded metal fibers control the expansion of the polymeric section from the unexpanded state to the expanded state, and determines the second larger diameter.

23. A method of plating an ablation burr with an abrasive, the ablation burr having a polymeric tube section with metal fiber embedded therein, the method comprising:
 providing the abrasive;
 removing a portion of the tube section of the ablation burr that overlays the embedded metal fiber to expose the embedded metal fiber; and
 plating the exposed embedded metal fiber with the abrasive.

* * * * *

UNITED STATES PATENT AND TRADEMARK OFFICE
CERTIFICATE OF CORRECTION

PATENT NO.     : 6,451,037 B1
DATED          : September 17, 2002
INVENTOR(S)    : V. Chandrasekaran et al.

It is certified that error appears in the above-identified patent and that said Letters Patent is hereby corrected as shown below:

<u>Title page,</u>
Item [56], References Cited, U.S. PATENT DOCUMENTS, delete the following references:
"B14,842,579 A  10/1995  Shiber"; and
"B14,990,134 A  11/1996  Auth".

Item [57], ABSTRACT,
Line 5, "into burr" should read -- into the burr --

<u>Column 6,</u>
Line 47, do not subindent the phrase beginning "an ablation burr having"
Line 50, do not subindent the phrase beginning " a polymeric tube extending"
Line 55, do not subindent the phrase beginning "metal fibers affixed"
Line 58, do not subindent the phrase beginning "an abrasive coating disposed"

<u>Column 7,</u>
Line 29, "portion the burr" should read -- portion of the burr --

<u>Column 8,</u>
Line 28, "determines" should read -- determine --

Signed and Sealed this

Twenty-seventh Day of May, 2003

JAMES E. ROGAN
*Director of the United States Patent and Trademark Office*